United States Patent [19]

Kroeker

[11] Patent Number: 4,903,636
[45] Date of Patent: Feb. 27, 1990

[54] ARTIFICIAL HABITAT FOR AQUATIC ANIMALS

[76] Inventor: James Kroeker, 2114 SW. 58 Ave., Hollywood, Fla. 33023

[21] Appl. No.: 66,952

[22] Filed: Jun. 29, 1987

[51] Int. Cl.$^4$ ............................................. A01K 61/00
[52] U.S. Cl. ........................................................ 119/3
[58] Field of Search .................................... 119/2, 3, 4

[56] References Cited

U.S. PATENT DOCUMENTS

| | | | |
|---|---|---|---|
| 883,418 | 10/1906 | Rückl | 119/3 |
| 3,486,486 | 12/1969 | Vanderborgh, Jr. et al. | 119/4 |
| 4,002,146 | 1/1977 | Neff | 119/3 X |
| 4,266,509 | 5/1981 | Gollott et al. | 119/3 X |
| 4,370,947 | 2/1983 | Hilken | 119/3 |
| 4,537,149 | 8/1985 | Ryan | 119/4 |
| 4,726,321 | 2/1988 | Malone et al. | 119/4 X |

Primary Examiner—Robert P. Swiatek
Attorney, Agent, or Firm—Herbert L. Lerner; Laurence A. Greenberg

[57] ABSTRACT

An artificial habitat for aquatic animals includes a frame defining an opening surrounded by the frame, a screen attached to the frame and covering the opening for supporting aquatic animals, the frame being supported with the screen at a given level, and water being circulated along at least part of the screen for removing waste from the screen.

10 Claims, 1 Drawing Sheet

4,903,636

ARTIFICIAL HABITAT FOR AQUATIC ANIMALS

SPECIFICATION:

The invention relates to an artificial habitat for maintaining live aquatic animals, such as certain aquatic worms including tubifex worms and earth worms, shrimps and gammarus, etc. in a live and healthy condition.

Aquatic animals are used as scientific research animals, tropical fish food, fish bait, bird food and animal food, etc..

In U.S. Pat. No. 867,138, a device for breeding silk worms is provided, in which enclosures having walls and floors formed of corn stalks are used to contain the worms. The enclosures lead through passageways to a receptacle for food.

U.S. Pat. No. 1,704,972 discloses a method and apparatus for conserving cocoons, in which the cocoons are moved between two chambers in which the temperature and humidity are regulated. Hampers formed of wire screen support the cocoons in the chambers to allow free circulation of air.

U.S. Pat. No. 1,717,227 provides a circulatory system in which air is cooled, dried and blown through a chamber in which cocoons are placed between two nets.

In U.S. Pat. No. 3,465,720, a plastic isolator for rearing silk worms is disclosed, in which the worms are placed in a plastic bag having an air inlet and outlet through which air is circulated in order to maintain a given air pressure and humidity.

All of these devices provide a habitat for silk worms which are land animals, not aquatic animals. Therefore, there is no need to provide an environment having water for maintaining the animals. In fact, most of the devices reduce humidity.

On the other hand, aquatic animals must be kept moist or they will not survive. There must also be provisions for removal of waste from the habitat, otherwise the animals contained therein will not survive.

It is accordingly an object of the invention to provide an artificial habitat for aquatic animals, which overcomes the hereinafore-mentioned disadvantages of the heretofore-known devices of this general type and which maintains the animals in a healthy, moist environment, while providing for removal of waste. The device should also be simple to construct and to use so that it can be used for distributors of aquatic animals as well as pet shops and residential and commercial consumers.

With the foregoing and other objects in view there is provided, in accordance with the invention, an artificial habitat for aquatic animals, comprising a frame defining an opening surrounded by the frame, a screen attached to the frame and covering the opening for supporting aquatic animals, means for supporting the frame with the screen at a given level, and means for circulating water along at least part of the screen for removing waste from the screen.

According to the invention, the screen supports the aquatic animals at the given level and the waste is removed by the circulating water.

In accordance with another feature of the invention, there is provided a tank containing water at the given level, the frame being part of an insert disposed in the tank.

The insert can be easily removed from the tank for removing and replacing animals and for cleaning.

In accordance with a further feature of the invention, the frame and the tank have upper ends, and the supporting means are in the form of a flange integral with the upper end of the insert, supporting the insert on the upper end of the tank with the screen at the given level.

The insert can be easily grasped from above by the flanges for removal.

In accordance with an added feature of the invention, the supporting means are in the form of a float connected to the insert and supporting the insert with the screen at the given level.

The float makes it possible to place the insert in any aquarium or tank of any size.

In accordance with an additional feature of the invention, the tank has a bottom, and the supporting means are in the form of a grating disposed on the bottom, the frame and the screen being supported on the grating with the screen at the given level.

The grating supports the screen without the screen sagging due to the weight of the animals.

In accordance with yet another feature of the invention, the grating includes screen supports spaced apart on the bottom of the tank.

In accordance with yet a further feature of the invention, the grating includes webs spacing the screen supports apart.

In accordance with yet an added feature of the invention, there is provided an inlet and an outlet feeding water into and out of the tank below the water level and producing a water current at the screen.

In accordance with yet an additional feature of the invention, the tank has oppositely disposed walls defining a given distance therebetween, the screen supports are shorter than the given distance, the screen supports have ends, the screen supports are adjacent one another in the tank, and the ends of adjacent screen supports abut opposite walls of the tank defining a serpentine path for water between the screen supports, and including an inlet and an outlet feeding water into and out of the tank below the water level and producing a water current at the screen along the serpentine path.

This feature provides excellent water circulation and waste removal.

In accordance with still another feature of the invention, the supporting means are in the form of blocks supporting the frame and the screen, and the circulating means are in the form of at least one nozzle spraying water on the screen.

This feature permits the screen to be supported above any surface.

In accordance with a concomitant feature of the invention, there is provided a tank containing water at the given level, the circulating means being in the form of an aerator disposed in the tank below the given level causing air bubbles to rise in the water and producing a water current along at least part of the screen.

An aerator is a simple yet effective means of providing a water current.

Other features which are considered as characteristic for the invention are set forth in the appended claims.

Although the invention is illustrated and described herein as embodied in an artificial habitat for aquatic animals, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

Figure 1:
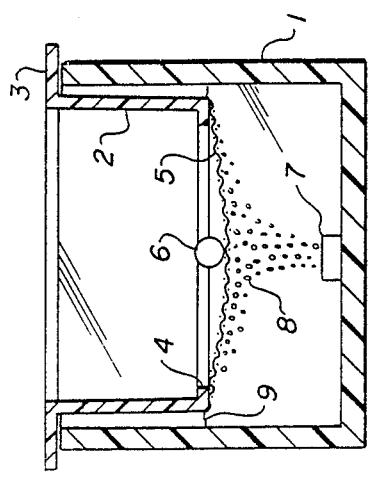
FIG. 1 is a diagrammatic, cross-sectional view of a first embodiment of the invention in the form of an insert suspended in a tank.
Figure 2:
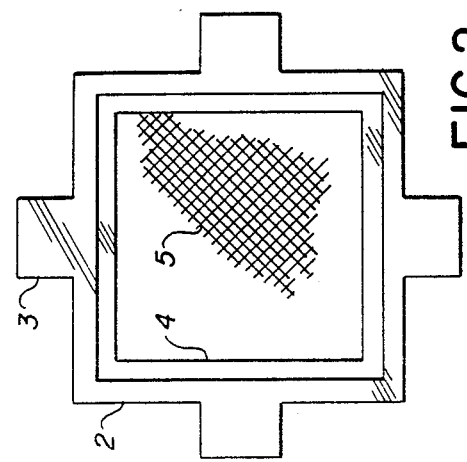
FIG. 2 is top-plan view of the insert of FIG. 1.

Referring now to the figures of the drawings in detail and first, particularly, to FIGS. 1 and 2 thereof, there is seen a tank 1 formed of transparent plastic. The tank may also be formed of glass and it may have a metal frame or it may be entirely formed of metal. The tank 1 is filled with water up to a level 9. An insert 2 is placed in the tank 1 from above, so that flanges 3 thereof rest on the upper surface of the tank and a frame 4 thereof is at the water level 9. The insert is also preferably formed of transparent plastic. A plastic screen 5 covers the opening surrounded by the frame and is adhesively connected to the lower surface of the frame 4 for supporting aquatic animals.

In the illustrated embodiment of FIG. 1, tubifex worms are placed on the screen 5. The tubifex worms naturally form a ball 6 having a diameter of approximately one inch, when approximately one ounce of worms are placed on the screen. Other aquatic animals have different weights but it appears to be critical that if a diameter of more than about one inch is used, the animals will be difficult to maintain alive. The ambient temperature also has an effect on the quantity of worms that can be maintained alive. This is because as the temperature becomes lower, the worms produce less waste and the accumulation of waste is an important factor leading to the death of the worms.

The weight of the worms causes the screen to dip slightly below the water level in the center, as shown. An aerator 7 which is placed on the bottom of the tank, but could be at any level below the water level 9, emits air bubbles 8 which diffuse upwardly and outwardly below the ball 6 of worms and the screen 5.

The air bubbles 8 maintain a constant water current below the worms and help to wash waste from the worms through the screen 5. Thus, the mesh openings of the screen must be small enough to prevent the worms from falling through, yet large enough to allow waste to fall through. The fineness of the screen can be chosen anywhere between these limits. Mesh with openings which are approximately 177 $\mu$ wide or slightly smaller, is preferred.

Figure 3:
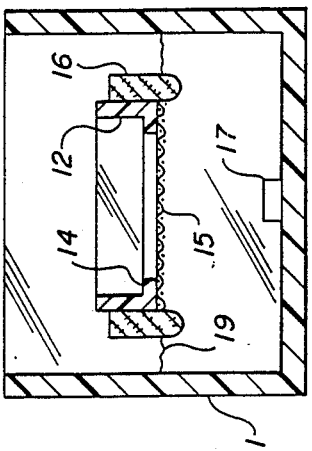
FIG. 3 is a cross-sectional view of a second embodiment in the form of a float in a tank.

According to the FIG. 3 embodiment, an insert 12 is provided which is almost identical to a lower portion of the insert 2, in that a screen 15 is connected to a frame 14 thereof. However, unlike the embodiment of FIG. 1, an annular float 16 suspends the insert 12 at a water level 19. An aerator 17 is also provided, but the bubbles and the worms on the screen have not been illustrated because they would appear exactly as shown in FIG. 1.

Figure 4:
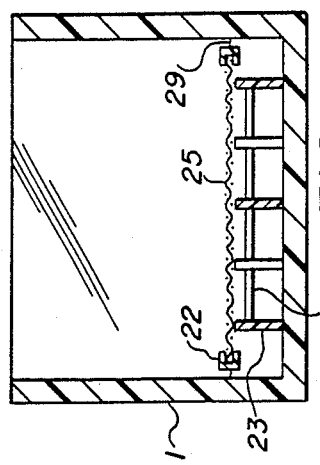
FIG. 4 is a cross-sectional view of a third embodiment of the invention in the form of an insert lying on the floor of a tank.
Figure 5:
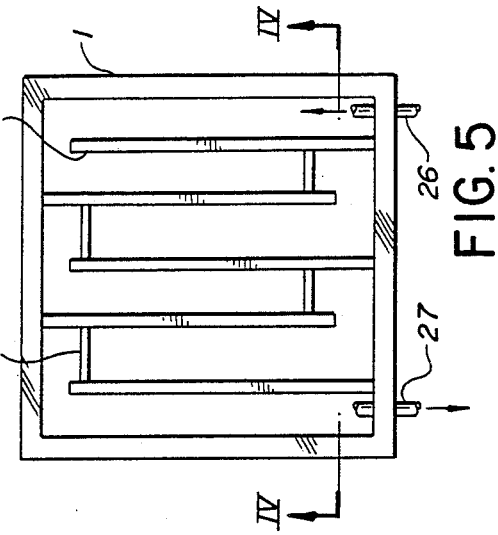
FIG. 5 is a top-plan view of the device of FIG. 4, with the screen removed.

In the embodiment of the invention shown in FIGS. 4 and 5, a grating is provided with screen supports 23 spaced apart on the bottom of the tank 1 by webs 24. A screen 25 in a frame 22 is placed at a water level 29 on the supports 23. The screen may be so heavy or stiff that the screen inherently includes a frame, thus making a separate frame unnecessary. The supports 23 are particularly advantageous because they prevent the screen from sagging, while allowing the screen to perform its waste removal function.

As shown in FIG. 5 in which the screen has been removed for the sake of clarity, a water inlet 26 and a water outlet 27 are disposed in the wall of the tank 1. FIG. 5 furthermore shows that all of the supports 23 are shorter than the depth of the tank 1 and they are placed against alternating walls of the tank, thus providing a serpentine path for the water current. The water flow provided by the inlet, outlet and supports serves to wash away waste from the worms, just as is done by the aerator of FIGS. 1 and 3, although the outlet actually can remove the waste from the tank, which must be done manually in the other embodiments. However, an aerator could still be used in conjunction with elements 23, 26 and 27 or it could be used with supports which were the full depth of the tank, while eliminating the inlet and outlet.

Figure 6:
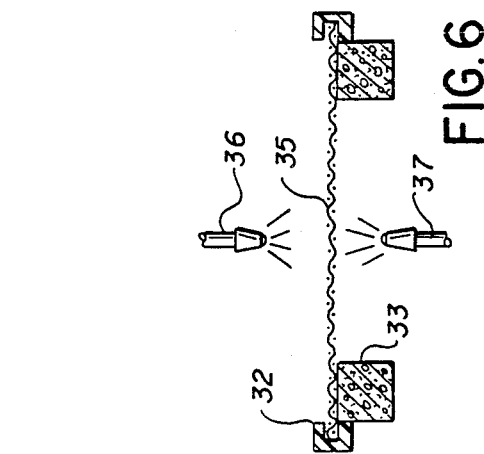
FIG. 6 is a cross-sectional view of a fourth embodiment of the device in which a screen is supported on blocks.

In the FIG. 6 embodiment, no tank is provided and instead a screen 35 with a frame 32 is simply supported on blocks 33. The screen may be so heavy or stiff that the screen inherently includes a frame, thus making a separate frame unnecessary. The blocks are formed of concrete but may also be wood or any other suitable material. Since no water level is maintained, the worms are kept moist by spraying water from above and/or below by water nozzles 36, 37. Naturally, the screen 35 may also be supported on supports 23 which may all be of the same length. The nozzles 36, 37 simply wash the waste onto the floor.

I claim:

1. Artificial habitat for aquatic worms, comprising a frame defining an opening surrounded by said frame, a screen attached to said frame and covering said opening for supporting aquatic worms, means for supporting said frame with said screen along a given water level such that the aquatic worms are partially above and partially below the given water level, and means for circulating water along at least part of said screen from below for supplying water to the worms and removing waste from said screen.

2. Artificial habitat according to claim 1, including a tank containing water at said given level, said frame being part of an insert disposed in said tank.

3. Artificial habitat according to claim 2, wherein said frame and said tank have upper ends, and said supporting means are in the form of a flange integral with said upper end of said frame, supporting said insert on said upper end of said tank with said screen at said given level.

4. Artificial habitat according to claim 3, including a tank containing water at said given level, said circulating means being in the form of an aerator disposed in said tank below said given level causing air bubbles to rise in the water and producing a water current along at least part of said screen.

5. Artificial habitat according to claim 2, wherein said supporting means are in the form of a float connected to said insert and supporting said insert with said screen at said given level.

6. Artificial habitat according to claim 5, including a tank containing water at said given level, said circulating means being in the form of an aerator disposed in said tank below said given level causing air bubbles to rise in the water and producing a water current along at least part of said screen.

7. Artificial habitat according to claim 1, including a tank containing water at said given level, said circulating means being in the form of an aerator disposed in said tank below said given level causing air bubbles to rise in the water and producing a water current along at least part of said screen.

8. Artificial habitat for aquatic animals, comprising a tank having a bottom and containing water at a given level, an insert disposed in said tank, said insert including a frame defining an opening surrounded by said frame, a screen attached to said frame and covering said opening for supporting aquatic animals, means in the form of a grating including screen supports spaced apart on said bottom of said tank for supporting said frame with said screen at said given level, said frame and said screen being supported on said grating with said screen at said given level, said tank having oppositely disposed walls defining a given distance therebetween, said screen supports being shorter than said given distance, said screen supports having ends, said screen supports being adjacent one another in said tank, and said ends of adjacent screen supports abutting opposite walls of said tank defining a serpentine path for water between said screen supports, and an inlet and an outlet feeding water into and out of said tank below said given water level and producing a water current at said screen along said serpentine path for removing waste from said screen.

9. Artificial habitat according to claim 8, wherein said grating includes webs spacing said screen supports apart.

10. Artificial habitat for aquatic worms, comprising a frame defining an opening surrounded by said frame, a screen attached to said frame and covering said opening for supporting aquatic worms, means for supporting said frame with said screen at a given level in the air, and means for circulating water along at least part of said screen for removing waste from said screen, said supporting means being in the form of blocks supporting said frame and said screen, and said circulating means being in the form of at least one nozzle spraying water on said screen.

* * * * *